US009581429B2

(12) United States Patent
Allier et al.

(10) Patent No.: US 9,581,429 B2
(45) Date of Patent: Feb. 28, 2017

(54) METHOD AND SYSTEM FOR RECONSTRUCTING OPTICAL PROPERTIES OF DIFFRACTING OBJECTS IMMERSED IN A LIQUID MEDIUM

(71) Applicant: Commissariat à l'énergie atomique et aux énergies alternatives, Paris (FR)

(72) Inventors: Cédric Allier, Grenoble (FR); Srikanth Vinjimore Kesavan, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/941,100

(22) Filed: Jul. 12, 2013

(65) Prior Publication Data

US 2014/0016137 A1     Jan. 16, 2014

(30) Foreign Application Priority Data

Jul. 13, 2012  (FR) ..................................... 12 56816

(51) Int. Cl.

| | |
|---|---|
| *G01B 9/02* | (2006.01) |
| *G01N 21/47* | (2006.01) |
| *G01N 21/45* | (2006.01) |
| G01N 15/14 | (2006.01) |
| G01N 15/10 | (2006.01) |
| G03H 1/04 | (2006.01) |

(52) U.S. Cl.
CPC ..... *G01B 9/02041* (2013.01); *G01N 15/1434* (2013.01); *G01N 21/45* (2013.01); *G01N 21/4788* (2013.01); *G03H 1/0443* (2013.01); G01N 2015/1006 (2013.01); G01N 2015/1454 (2013.01); G03H 2001/0447 (2013.01)

(58) Field of Classification Search
CPC .................................................. G01B 9/02041
USPC ......................................................... 356/437
See application file for complete search history.

(56) References Cited

U.S. PATENT DOCUMENTS

| | | | |
|---|---|---|---|
| 2011/0027825 A1* | 2/2011 | Larsen ............... | G01N 15/1227 435/39 |
| 2011/0136165 A1* | 6/2011 | Vojnovic et al. ............... | 435/39 |
| 2012/0044320 A1* | 2/2012 | Spivey ................. | G03H 1/0443 348/40 |

OTHER PUBLICATIONS

Search Report for FR 1256816 dated Mar. 20, 2013.
Fienup, "Phase Retrieval Algorithms: A Comparison", Applied Optics, 1982, pp. 2758-2769, vol. 21, No. 15.

(Continued)

*Primary Examiner* — Tarifur Chowdhury
*Assistant Examiner* — Omar Nixon
(74) *Attorney, Agent, or Firm* — Thompson Coburn LLP

(57) ABSTRACT

A method for reconstructing optical properties of a diffracting object immersed in a liquid medium using a reconstruction system that comprises a spatially coherent light source and a matrix photodetector, wherein the liquid medium and the matrix photodetector are separated by a distance along a vertical direction. The method comprises illuminating the liquid medium, measuring (with the matrix photodetector) an intensity of a diffraction pattern transmitted by the illuminated medium along a vertical direction, and reconstructing the optical properties of the diffracting object at a reconstruction height according to a reconstruction algorithm from the measured intensity, wherein the reconstruction height has a value less than that of the distance between the medium and the matrix photodetector along the vertical direction.

17 Claims, 10 Drawing Sheets

(56) References Cited

OTHER PUBLICATIONS

Seo et al., "Lensfree Holographic Imaging for On-Chip Cytometry and Diagnostics", Lab on a Chip, Royal Society of Chemistry, 2009, pp. 777-787, vol. 9.
Denis et al., "Twin-Image Noise Reduction by Phase Retrieval in In-Line Digital Holography", Wavelets XI, SPIE's Symposium on Optical Science and Technology, 2005, pp. 1-15, San Diego, CA.

* cited by examiner

METHOD AND SYSTEM FOR RECONSTRUCTING OPTICAL PROPERTIES OF DIFFRACTING OBJECTS IMMERSED IN A LIQUID MEDIUM

CROSS-REFERENCE TO RELATED APPLICATIONS

The present application is a non-provisional application claiming the benefit of French Application No. 12 56816, filed Jul. 13, 2012, which is incorporated herein by reference in its entirety.

FIELD OF THE INVENTION

The invention relates to lensless imaging (i.e. the acquisition, by a matrix photodetector, of images formed by the radiation directly transmitted by the medium, in the absence of magnification optics positioned between the medium and the matrix photodetector). More specifically, the invention relates to a system and method for reconstructing optical properties of diffracting objects immersed in a liquid medium.

BACKGROUND OF INVENTION

A method for reconstructing optical properties of diffracting objects by means of a lensless imaging device is known from the article entitled, *Lensfree in-line holographic detection of bacteria*, Poher et al. In this method, dust particles are placed on the surface of a protective cap, located at about 400 µm from a CMOS (Complementary Metal Oxide Semiconductor) sensor, the dust particles are illuminated with a spatially coherent light source, and the CMOS sensor measures the intensity of the diffraction patterns corresponding to waves diffracted by the dust particles when they are illuminated. The complex amplitude of the dust particles is reconstructed, according to a reconstruction algorithm, from the measured intensity, the reconstruction algorithm depending on a reconstruction height. The reconstruction height is substantially equal to the height of the protective cap of the CMOS sensor (i.e., substantially equal to the distance between the dust particles and the CMOS sensor along the illumination direction of the particles). However, such a reconstruction method does not allow access to more specific information, notably relating to the structure of the observed particles. Thus, when the observed particles are cells, this method does not give the possibility of distinguishing and viewing the nucleus from the cytoplasm of a single cell.

Thus, a need still exists for a method and system of reconstructing optical properties of diffracting objects, for objects having a diameter of less than 50 µm, notably cells, or colonies of bacteria, giving the possibility of obtaining more specific information on said objects.

SUMMARY OF INVENTION

The invention is directed to a method for reconstructing optical properties of at least one diffracting object immersed in a liquid medium using a reconstruction system that comprises a spatially coherent light source and a matrix photodetector, wherein the liquid medium is delimited by a transparent surface and the at least one diffracting object is in contact with the transparent surface, and wherein the liquid medium and the matrix photodetector are separated by a distance along a vertical direction, the method comprising:

illuminating the liquid medium with the spatially coherent light source;

measuring, with the matrix photodetector, an intensity of at least one diffraction pattern transmitted by the illuminated medium along a vertical direction, wherein each diffraction pattern corresponds to waves diffracted by the at least one diffracting object upon illumination of the medium; and reconstructing the optical properties of the at least one diffracting object at a reconstruction height according to a reconstruction algorithm from the measured intensity, wherein the reconstruction height has a value less than that of the distance between the medium and the matrix photodetector along the vertical direction.

The invention is also directed to a system for reconstructing optical properties of at least one diffracting object immersed in a liquid medium, the liquid medium being delimited by a transparent surface, the at least one diffracting object being in contact with the transparent surface, the reconstruction system comprising:

a spatially coherent light source capable of illuminating the medium;

a matrix photodetector separated from the liquid medium by a distance along a vertical direction, wherein the matrix photodetector is capable of measuring an intensity of at least one diffraction pattern transmitted by the illuminated medium along a vertical direction, and wherein said at least one diffraction pattern corresponds to waves diffracted by the at least one diffracting object upon illumination of the medium; and a means for reconstructing the optical properties of the at least one diffracting object at a reconstruction height according to a reconstruction algorithm from the measured intensity, wherein the reconstruction height has a value less than that of the distance between the medium and the matrix photodetector along the vertical direction.

BRIEF DESCRIPTION OF THE DRAWINGS

The features and advantages of the invention will become apparent upon reading the description which follows, only given as a non-limiting example, and made with reference to the appended drawings.

DETAILED DESCRIPTION OF INVENTION

Figure 1:
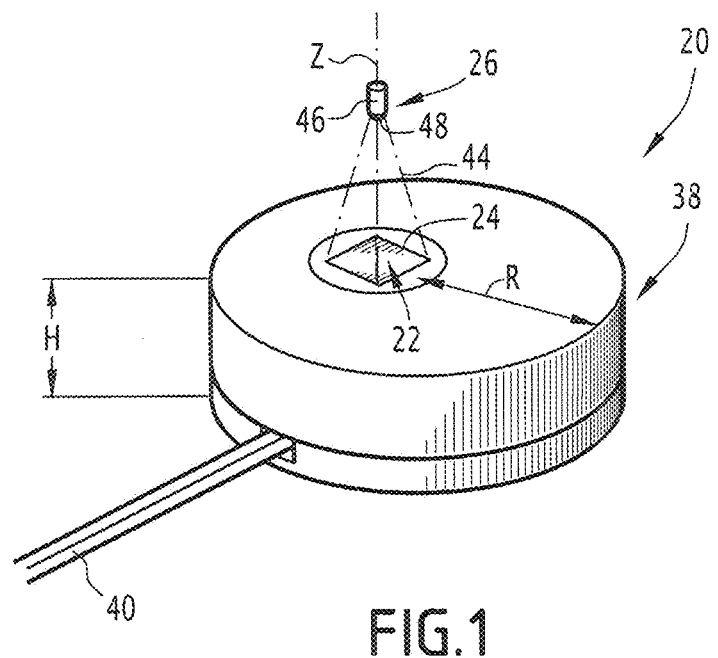
FIG. 1 is a perspective view of a reconstruction system according to the invention.

In one embodiment, the present invention is directed to a method for reconstructing optical properties of diffracting objects immersed in a liquid medium, the liquid medium being delimited by a transparent surface and the diffracting objects being in contact with the transparent surface. The reconstruction method comprises: illumination of the medium by the spatially coherent light source; measurement by the matrix photodetector of an intensity of at least one diffraction pattern transmitted by the illuminated medium along a vertical direction, said or each diffraction pattern corresponding to waves diffracted by one or several diffracting objects upon illumination of the medium; and reconstruction of the optical properties of the objects, according to the reconstruction algorithm, from the measured intensity and depending on the reconstruction height. In other words, the reconstruction of the optical properties is carried out at the reconstruction height.

In one embodiment, the present invention is directed to a system for reconstructing optical properties, comprising a spatially coherent light source, a matrix photodetector and means for reconstructing optical properties of the objects, according to a reconstruction algorithm, from the measured intensity and depending on a reconstruction height.

The term "optical properties" is intended to include the absorption of the object or the phase lag introduced by the object, being aware that these parameters represent the modulus and the argument of the complex opacity function of the object, respectively. With the invention it is notably possible to determine the spatial distribution of these parameters.

The term "lensless imaging device" is used herein alternatively to the term "matrix photodetector" and is capable of forming an image of the medium by being placed at a small distance from the latter. By small distance, is meant a distance comprised between 100 μm and a few centimeters, preferably less than 1 cm.

The invention is particularly useful for the reconstruction of optical properties of particles, notably biological particles, such as cells, bacteria, and viruses, which have sizes on the order of 10 μm for cells and 1 μm for bacteria.

As indicated above, the method for reconstructing optical properties of diffracting objects immersed in a liquid medium uses a reconstruction system comprising a spatially coherent light source and a matrix photodetector, the liquid medium being delimited by a transparent surface. The diffracting objects being in contact with the transparent surface. The reconstruction method comprising the following steps:

illumination of the medium by the spatially coherent light source;

measurement by the matrix photodetector, of an intensity from at least one diffraction pattern transmitted by the illuminated medium along a vertical direction, said or each diffraction pattern corresponding to waves diffracted by one or several diffracting objects upon illumination of the medium;

reconstruction of the optical properties of the objects, according to a reconstruction algorithm, from the measured intensity, the reconstruction algorithm depending on a reconstruction height; and wherein during the reconstruction step, the reconstruction height has a value strictly less than that of the distance between the medium and the matrix photodetector along the vertical direction, preferably less than 0.9 times said distance between the medium and the photodetector, still preferably less than 0.8 times said distance.

According to other advantageous aspects of the invention, the reconstruction method comprises one or several of the following features, taken individually or according to all the technically possible combinations:

during the reconstruction step, the reconstruction algorithm satisfies the following equation:

$$I(x, y) * h_{-Zr}(x, y) = e^{j2\pi\frac{-Zr}{\lambda}}\left(1 - a(x, y) - e^{j2\pi\frac{2Zr}{\lambda}} \cdot a^*(x, y) * h_{-2Zr}(x, y)\right)$$

wherein I represents the intensity measured by the matrix photodetector, x, y represents the coordinates in a plane perpendicular to the vertical direction, * designates the convolution product, Zr represents the reconstruction height, λ represents the wave length of the light source, j represents the unit imaginary number, a represents the complex opacity function of an object, a* represents the conjugate complex of a, and $h_z$ is defined by the following equation:

$$h_z(x, y) = \frac{1}{j\lambda z} e^{j2\pi\frac{z}{\lambda}} \exp\left(j\pi\frac{x^2 + y^2}{\lambda z}\right);$$

during the reconstruction step, the optical properties of the objects are reconstructed for different values of the reconstruction height, each being strictly less than the value of the distance between the medium and the matrix photodetector along the vertical direction;

at least one object includes a first structure and a second structure, and the optical properties of the first structure are reconstructed for a first value of the reconstruction height, and the optical properties of the second structure are reconstructed for a second value of the reconstruction height, the second value being distinct from the first value;

the object is a cell including a nucleus and a cytoplasm, and a representative image of the nucleus is reconstructed for a first interval of values and a representative image of the cytoplasm is reconstructed for a second interval of values, the second interval being distinct from the first interval, the second interval being preferably disconnected from the first interval, the values of the first interval being still preferably less than that of the second interval;

the distance between the medium and the matrix photodetector along the vertical direction is substantially equal to 500 µm, the first interval is the interval of values comprised between 240 µm and 280 µm, and the second interval is the interval of the values comprised between 380 µm and 420 µm;

the intensity of said or each diffraction pattern is directly measured by the matrix photodetector, in the absence of any magnification optics placed between the medium and the photodetector; and the reconstructed optical properties include the absorption of the object and/or the phase lag produced by the object.

The subject-matter of the invention is also a system for reconstructing optical properties of diffracting objects immersed in a liquid medium, the liquid medium being delimited by a transparent surface, the diffracting objects being in contact with the transparent surface, the reconstruction system comprising:

a spatially coherent light source, capable of illuminating the medium;

a matrix photodetector, capable of measuring an intensity of at least one diffraction pattern transmitted by the illuminated medium along a vertical direction, said or each diffraction pattern corresponding to waves diffracted by one or several diffracting objects upon illumination of the medium; and means for reconstructing the optical properties of the objects, according to a reconstruction algorithm, from the measured intensity, the reconstruction algorithm depending on a reconstruction height, the reconstruction height having a value strictly less than that of the distance between the medium and the matrix photodetector along the vertical direction, preferably less than 0.9 times said distance between the medium and the photodetector, still preferably less than 0.8 times said distance.

According to other advantageous aspects of the invention, the reconstruction system comprises one or several of the following features, taken individually or according to all the technically possible combinations:

(a) the light source includes a light-emitting diode and a diaphragm placed in contact with the light-emitting diode; and (b) the matrix photodetector is a CCD sensor or a CMOS sensor.

Figure 2:
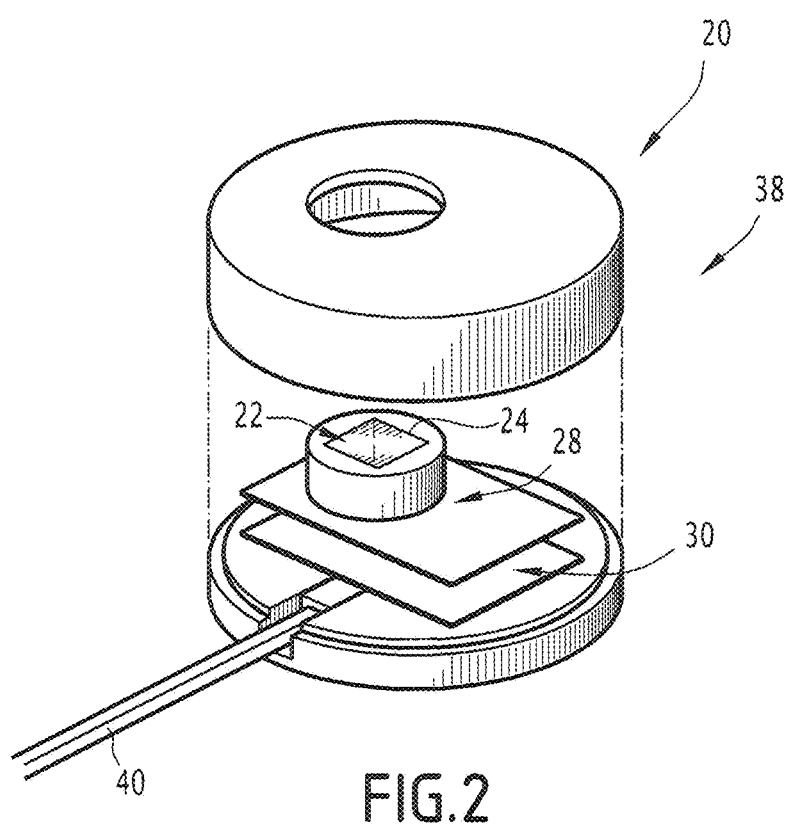
FIG. 2 is an exploded view of the reconstruction system of FIG. 1.

In FIGS. 1 and 2, a system 20 for reconstructing optical properties of diffracting objects 22 immersed in a liquid medium 24, comprises a spatially coherent light source 26 and a matrix photodetector 28.

Figure 3:
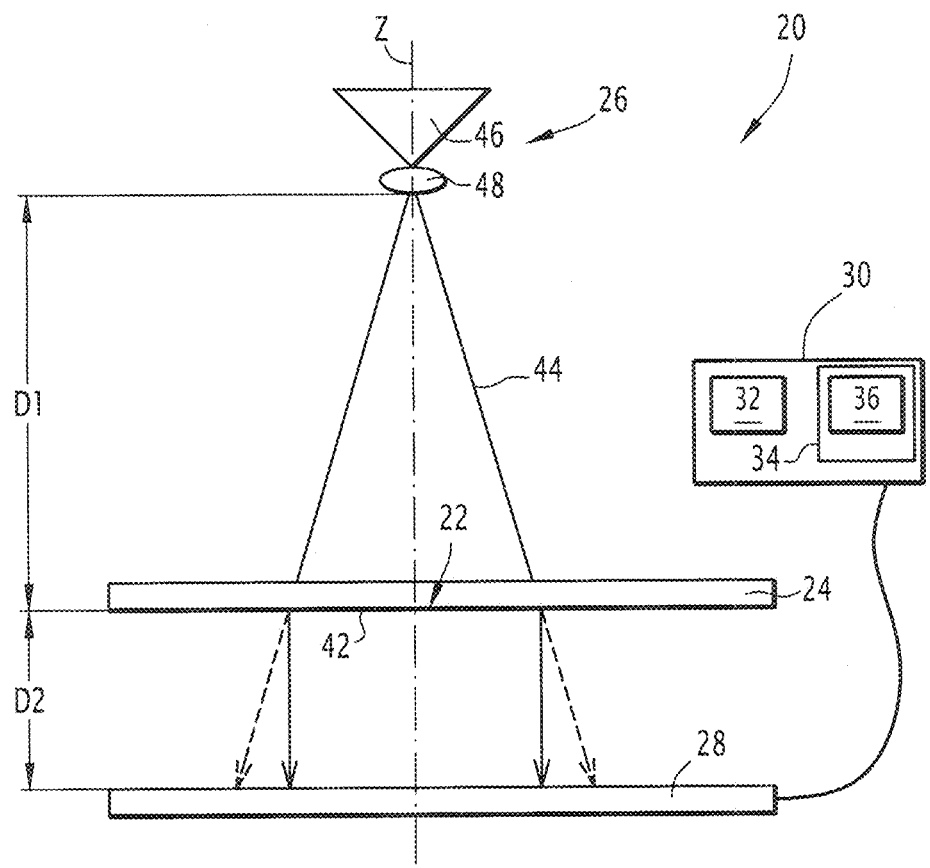
FIG. 3 is a schematic illustration of the reconstruction system of FIG. 1, the reconstruction system comprising a light source, a matrix photodetector and means for reconstructing optical properties of the objects.

The reconstruction system 20 also comprises an information processing unit 30, visible in FIG. 3, including a processor 32 and a memory 34 capable of storing a software package 36 for reconstructing optical properties of the diffracting objects 22, the optical properties being reconstructed according to a reconstruction algorithm from an intensity I measured by the photodetector 28.

The reconstruction system 20 comprises a protective housing 38, visible in FIGS. 1 and 2, inside which are notably placed the photodetector 28 and the information processing unit 30. The reconstruction system 20 comprises an electric power supply wire link 40.

The diffracting objects 22 for example are particles, such as biological particles, i.e. cells (for example red corpuscles, white corpuscles or platelets), bacteria or bacterial colonies, cells or aggregates of cells. Alternatively, the diffracting particles 22 are microbeads.

The diffracting objects 22 preferably have a diameter of less than 20 µm. The diameter of the diffracting objects 22 is for example comprised between 100 nm and 10 µm. The bacteria have a diameter of the order of 1 µm and the cells have a diameter of the order of 10 µm.

Figures 8, 9:
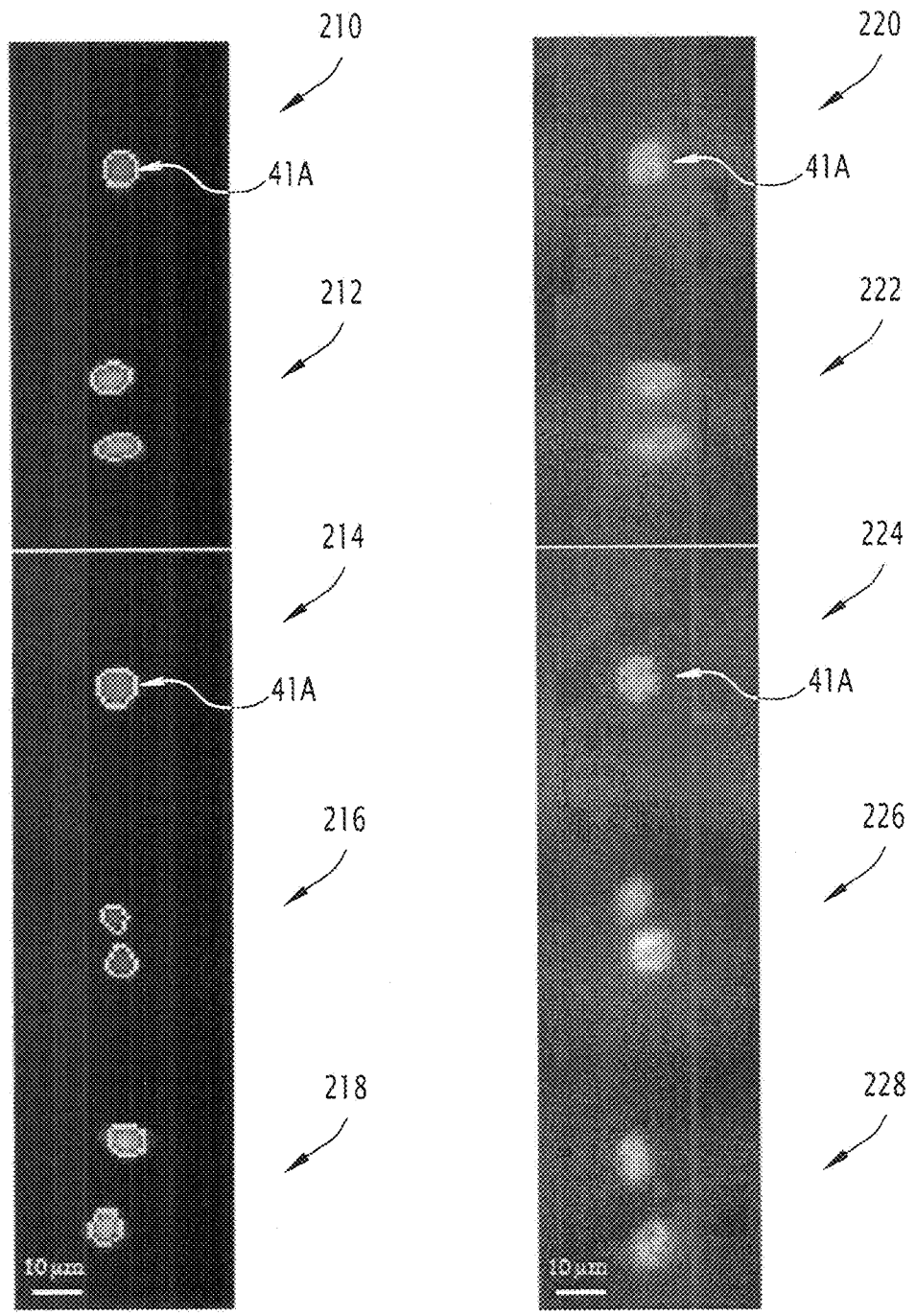
FIG. 8 is a view of the respective images of the first structures of the five objects of FIG. 7, for a reconstruction height in a first interval of values comprised between 280 μm and 350 μm.
FIG. 9 is a view of the respective reference images of the first structures of the five objects of FIG. 7, the reference images being obtained by use of a microscope.
Figure 10:
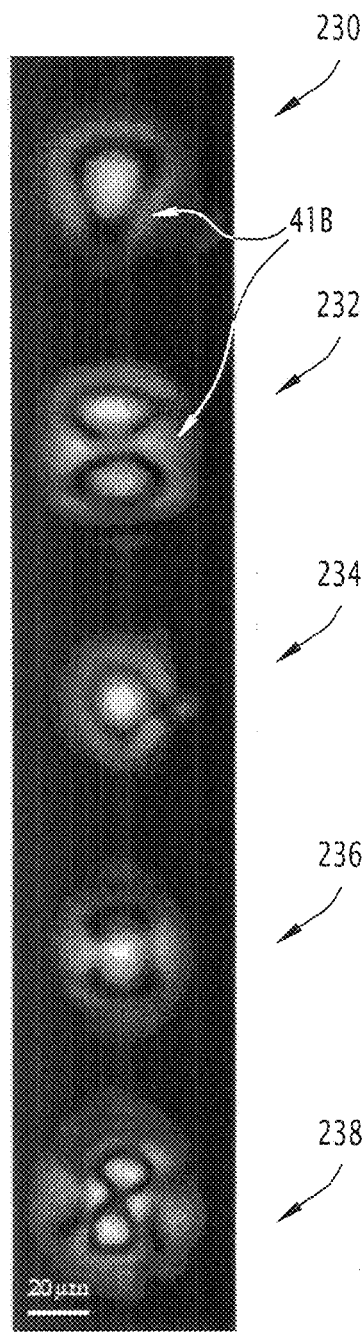
FIG. 10 is a view of the respective images of the second structures of the five objects of FIG. 7, for a reconstruction height in a first interval of values comprised between 410 μm and 450 μm.
Figure 11:
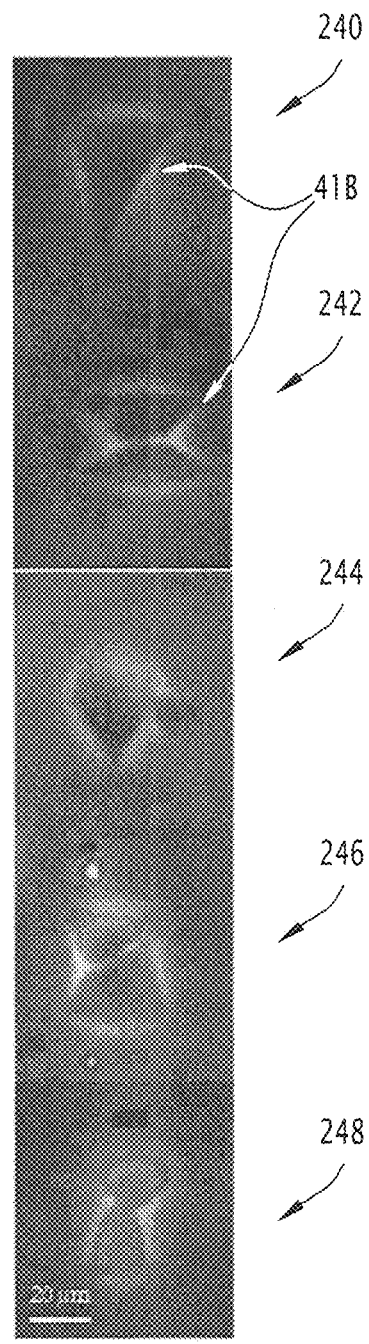
FIG. 11 is a view of the respective reference images of the second structures of the five objects of FIG. 7, obtained by use of a microscope.

The object 22 comprises a first structure 41A and a second structure 41B, visible in FIGS. 8 and 9, respectively in FIGS. 10 and 11. In the exemplary embodiment of FIGS. 8 to 11 wherein the object 22 is a cell, the first structure 41A is a nucleus and the second structure 41B is a cytoplasm.

The liquid medium 24 is delimited by a transparent surface 42, visible in FIG. 3. The diffractive objects 22 are in contact with said transparent surface 42.

The medium 24 is placed between the light source 26 and the matrix photodetector 28, and is substantially perpendicular to a vertical direction Z corresponding to the illumination direction of the medium by the light source 26, as illustrated in FIG. 3.

The light source 26 is capable of emitting a light beam 44 along the vertical direction Z, in order to illuminate the liquid medium 24 comprising the diffracting objects 22.

The light source 26 is placed at a first distance D1 from the transparent surface 42 along the vertical direction Z. The first distance D1 preferably has a value comprised between 1 cm and 30 cm, for example equal to 8 cm.

The light source 26 is a spatially coherent source. The light source 26 for example includes a point-like source such as a light-emitting diode 46, also called LED, and a diaphragm 48 placed in contact with the LED 46, as illustrated in FIG. 3. The diaphragm 48 has a diameter comprised between 50 µm and 500 µm, and is placed in contact with the light source 26. This gives the possibility of increasing the spatial coherence of the light radiation.

Alternatively, the light source 26 consists of the light-emitting diode 46, and does not include any diaphragm. The light-emitting diode 46 then has sufficiently reduced dimensions so as to be considered as spatially coherent, the diameter of the light-emitting diode 46 being less than one tenth of the first distance D1 separating this light-emitting diode from the transparent surface 42.

Still alternatively, the light source 26 is a spatially and temporally coherent light source, for example a laser diode (DL) or further a laser diode of the VCSEL (Vertical Cavity Surface Emitting Laser) type.

The matrix photodetector 28 includes a plurality of pixels, not shown. Each pixel of the photodetector 28 has dimensions of less than or equal to 10 µm, or even 4 µm. Each pixel is for example square-shaped, the side of which is of a value of less than or equal to 10 µm, or even 4 µm. Alternatively, each pixel has the shape of a square with a side of 2.2 µm.

The photodetector 28 is placed at a second distance D2 from the transparent surface 42 along the vertical direction Z. The second distance D2 has a value comprised between 100 µm and a few centimeters, preferably less than 1 cm, and still preferably comprised between 100 µm and 2 mm. In the described exemplary embodiment, the second distance D2 is equal to 700 µm.

By giving preference to a second distance D2 of small value, i.e. a short distance between the matrix photodetector 28 and the transparent surface 42, it is possible to limit the interference phenomena between different diffraction patterns when the medium 24 is illuminated.

The matrix photodetector 28 is capable of acquiring images of the radiation transmitted by the medium 24 containing the diffracting objects 22 illuminated by the light beam 44. By transmitted radiation is meant the radiation crossing the medium 24 so that the matrix photodetector 28 and the light source 26 are located on either side of the medium 24 and of the diffracting objects 22.

The matrix photodetector 28 is a two-dimensional image sensor, i.e. in a plane perpendicular to the longitudinal axis X. The matrix photodetector 28 is a pixelated image sensor, for example a CMOS sensor. Alternatively, the matrix photodetector 28 is a CCD (Charged-Coupled Device) sensor.

The matrix photodetector 28 additionally includes microlenses, not shown, each microlens being placed above a corresponding pixel. Such microlenses are integrated into the sensor. They allow improvement in the collection yield and do not form magnification optics placed between the transparent surface 42 and the photodetector 28.

The images acquired by the matrix photodetector 28 are formed by the radiation directly transmitted by the illuminated medium 24, in the absence of any magnification optics placed between the transparent surface 42 and the matrix photodetector 28. The photodetector 28 is also called a lensless imaging device, and is capable of forming an image of the medium 24, while being placed at a small distance from the latter. By small distance, is meant as indicated earlier, a distance of less than a few centimeters, preferably less than 1 cm, the second distance D2 being for example equal to 700 µm.

The matrix photodetector 28 is capable of measuring the intensity I of at least one diffraction pattern transmitted by the medium 24, said or each diffraction pattern corresponding to waves diffracted by one or several diffracting objects 22 upon illumination of the medium 24.

The reconstruction software package 36 is capable of reconstructing the optical properties of the diffracting objects 22, according to the reconstruction algorithm, from the measured intensity I. The reconstruction algorithm depends on a reconstruction height Zr. In other words, the reconstruction of the optical properties is carried out with a height along the vertical direction Z, equal to the reconstruction height Zr.

According to the invention, and unlike the state of the art, the reconstruction height Zr has a value strictly less than that of the second distance D2 between the transparent surface 42 and the matrix photodetector 28 along the vertical direction Z. The reconstruction height Zr is preferably less than 0.9 times the second distance D2, still preferably less than 0.8 times the second distance D2.

In the state of the art, the reconstruction height Zr is usually equal to the distance between the object to be observed and the sensor array, or even greater than this distance between the object and the sensor array.

The inventors surprisingly noticed that when the reconstruction height Zr, is according to the invention, strictly less than the second distance D2, i.e. the distance between the object 22 and the sensor array 28, preferably less than 0.9 times the second distance D2, this allows reconstruction of the optical properties of structures making up the diffracting objects 22, and notably reconstruction of the optical properties of the first structure 41A and/or of the second structure 41B of said objects 22.

According to an additional aspect of the invention, the optical properties of the first structure 41A are reconstructed for a first value Zr1 of the reconstruction height, and the optical properties of the second structure 41B are reconstructed for a second value Zr2 of the reconstruction height, the second value Zr2 being distinct from the first value Zr1. In the following examples, the reconstructed optical property is the absorption of the particle, in other words the modulus of the complex opacity function as defined hereafter. Each reconstructed image then represents the spatial distribution of the absorption in the reconstruction plane. The higher the grey level, the higher is the absorption.

In the exemplary embodiment of the diffracting cells 22, a representative image of a structure 41A is reconstructed for a first interval of values comprised between a first minimum value Zr1min and a first maximum value Zr1max. A representative image of the cytoplasm 41B is reconstructed for a second interval of values comprised between a second minimum value Zr2min and a second maximum value Zr2max.

The second interval [Zr2min; Zr2max] is distinct from the first interval [Zr1min; Zr1max], the second interval [Zr2min; Zr2max] being preferably disconnected from the first interval [Zr1min; Zr1max]. The values of the first interval [Zr1min; Zr1max] are still preferably less than those of the second interval [Zr2min; Zr2max]. In other words, the first maximum value Zr1max is less than the second minimum value Zr2min.

When the second distance D2 between the medium 24 and the matrix photodetector 28 along the vertical direction Z is substantially equal to 700 µm, the first interval [Zr1min; Zr1max] is the interval of values comprised between 280 µm and 350 µm, and the second interval [Zr2min; Zr2max] is the interval of values comprised between 410 µm and 450 µm.

Alternatively, when the second distance D2 is substantially equal to 500 µm, the first interval [Zr1min; Zr1max] is the interval of values comprised between 240 µm and 280 µm, and the second interval [Zr2min; Zr2max] is the interval of values comprised between 380 µm and 420 µm.

Alternatively, when the second distance D2 is substantially equal to 2,000 µm, the first interval [Zr1min; Zr1max] is the interval of values comprised between 1,200 µm and 1,300 µm, and the second interval [Zr2min; Zr2max] is the interval of values comprised between 1,400 µm and 1,500 µm.

The reconstruction algorithm is known per se, and satisfies the following equation:

$$I(x, y) * h_{-Zr}(x, y) = e^{j2\pi \frac{-Zr}{\lambda}} \left( 1 - a(x, y) - e^{j2\pi \frac{2Zr}{\lambda}} \cdot a^*(x, y) * h_{-2Zr}(x, y) \right) \quad (1)$$

wherein I represents the intensity measured by the matrix photodetector 28, x, y represent the coordinates in a plane perpendicular to the vertical direction Z, * designates the convolution product, Zr represents the reconstruction height, $\lambda$ represents the wavelength of the light source 26, j represents the unit imaginary number, a represents the complex opacity function of an object 22, a* represents the conjugated complex of a, and $h_z$ is defined by the following equation:

$$h_z(x, y) = \frac{1}{j\lambda z} e^{j2\pi \frac{z}{\lambda}} \exp\left(j\pi \frac{x^2 + y^2}{\lambda z}\right). \quad (2)$$

Equation (1) shows that the reconstruction algorithm is applied with a height z, along the vertical direction Z, equal to the reconstruction height Zr. Equation (1) is obtained from the following equations:

$$A_z(x,y) = t(x,y) * h_z(x,y) \quad (3)$$

wherein $A_z$ is the Fresnel transform of the transmittance t(x,y). Absorption coefficients a(x,y) and transmission coefficients t(x,y) are then defined in the following way:

$$t(x, y) = (1 - a(x, y)) \quad (4)$$

$$A_z(x, y) = t(x, y) * h_z(x, y) = (1 - a(x, y)) * h_z(x, y) = \quad (5)$$
$$1 * h_z(x, y) - a(x, y) * h_z(x, y) = e^{j2\pi \frac{z}{\lambda}} - a(x, y) * h_z(x, y)$$

The intensity I is then defined in the following way:

$$I = A \cdot A^* = 1 - e^{j2\pi \frac{z}{\lambda}} \cdot a^* * h_z^* - e^{-j2\pi \frac{z}{\lambda}} \cdot a * h_z + (a * h_z) \cdot (a^* * h_z^*) \quad (6)$$

The dual properties of the Fresnel transform corresponding to the following equations:

$$h_z^{**}*h_z = h_{-z}*h_z$$

$$h_z^**h_z = h_{2z} \quad (7)$$

then allow the reconstruction Equation (1) to be obtained:

$$I * h_{-z} \approx \left(1 - e^{j2\pi \frac{z}{\lambda}} \cdot a^* * h_z^* - e^{-j2\pi \frac{z}{\lambda}} \cdot a * h_z\right) * h_{-z} \quad (8)$$
$$I * h_{-z} = e^{j2\pi \frac{-z}{\lambda}} - e^{j2\pi \frac{z}{\lambda}} \cdot a^* * h_z^* * h_{-z} - e^{-j2\pi \frac{z}{\lambda}} \cdot a * h_z * h_{-z}$$
$$I * h_{-z} = e^{j2\pi \frac{-z}{\lambda}} - e^{j2\pi \frac{z}{\lambda}} \cdot a^* * h_{-z} * h_{-z} - e^{-j2\pi \frac{z}{\lambda}} \cdot a$$
$$I * h_{-z} = e^{j2\pi \frac{-z}{\lambda}} \left(1 - a - e^{j2\pi \frac{2z}{\lambda}} \cdot a^* * h_{-2z}\right)$$

From the measured image I(x,y), the complex opacity function a(x,y) is easily obtained according to usual algorithms, described in the literature, and in particular in the publication, *Twin-image noise reduction by phase retrieval in inline digital holography*, SPIES's Symposium on Optical Science and Technology, 2005. A simple algorithm is detailed as an example at the end of the specification.

The protective housing 38 is for example cylinder-shaped, as illustrated in FIGS. 1 and 2. The protective housing 38 has a height H along the vertical direction Z, and a radius R along a radial direction perpendicular to the vertical direction Z. The height H and the radius R of the housing 38 are for example centimetric.

The transparent surface 42 is preferably functionalized in order to allow better adherence of the diffracting objects 22 to the surface 42. By functionalization of the transparent surface 42 is meant a preparation of the surface 42 in order to allow this better adherence of the diffracting objects 22 to the surface 42. Fibromectin proteins are for example deposited on the surface 42 after plasma cleaning the surface 42 beforehand, and then with soda. Alternatively, other known functionalization techniques are applied, such as the use of an antigen-antibody, the use of DNA.

The transparent surface 42 for example has the shape of a transparent slide, having a thickness substantially equal to 170 µm along the vertical direction Z.

The light beam 44 is capable of directly illuminating the medium 24 and the objects 22, in the absence of any magnification optics placed between the light source 26 and the medium 24.

The light-emitting diode 46 is for example monochromatic with a bandpass width for example comprised between 20 nm and 40 nm, preferably equal to 30 nm. The light-emitting diode 46 for example has an emission wavelength comprised between 500 nm and 520 nm and a power of the order of a Watt.

The diaphragm 48 has a diameter with a value for example comprised between 50 µm and 700 µm, for example equal to 500 µm, or further equal to 80 µm.

Figure 4:
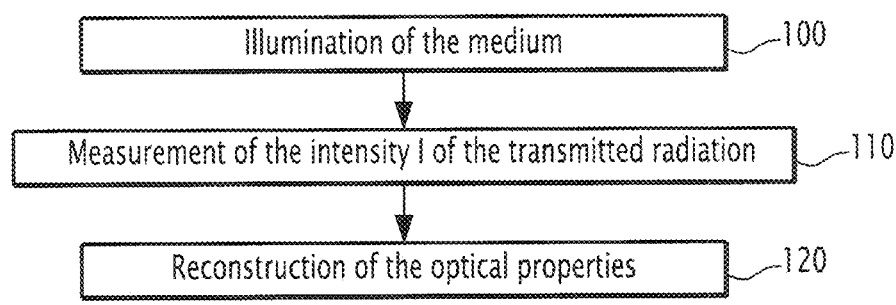
FIG. 4 is a flow chart of a reconstruction method according to the invention.

The reconstruction method according to the invention will now be described by means of FIG. 4.

During the initial step 100, the liquid medium 24 is illuminated by means of the spatially coherent light source 26, the light beam 44 being directed along the vertical direction Z.

The intensity I of the radiation transmitted by the illuminated medium 24 is then measured during step 110 with the matrix photodetector 28. More specifically, the matrix photodetector 28 measures the intensity I of the diffraction patterns transmitted by the illuminated medium 24, each diffraction pattern corresponding to waves diffracted by the diffracting objects 22 upon illumination of the medium 24, these diffracted waves interfering with the incident wave.

The optical properties, notably the absorption and the phase lag of the diffracting objects 22 are finally reconstructed during step 120, with reconstruction means 36, according to the reconstruction algorithm described earlier and from the measured intensity I. The phase lag corresponds to the argument of the complex opacity function a; the absorption corresponds to the modulus of the complex opacity function as defined earlier. Generally, a reconstruction image represents the spatial distribution of the absorption or of the phase lag.

As indicated earlier, the reconstruction height Zr has a value strictly less than that of the second distance D2 corresponding to the distance along the vertical direction Z between the medium 24 and the matrix photodetector 28, preferably less than 0.9 times the second distance D2, still preferably less than 0.8 times the second distance D2.

Generally, one refers to a reconstructed object 22 or reconstructed structure 41A, 41B for designating an object 22 or a structure 41A, 41B, the optical properties of which are reconstructed according to the reconstruction algorithm.

According to a complementary aspect, the optical properties of the objects 22 are reconstructed for different values of the reconstruction height Zr, each being strictly less than the value of the second distance D2.

In the described exemplary embodiment, the reconstruction software package 36 varies, during the reconstruction step 120, the value of the reconstruction height Zr between the zero value and a predetermined value strictly less than the second distance D2. The said predetermined value of the reconstruction height Zr is for example equal to 0.9 times the second distance D2.

Additionally, the optical properties of the first structure 41A are reconstructed for the first value Zr1 of the reconstruction height, or even for the first interval of values [Zr1min; Zr1max]. The optical properties of the second structure 41B are reconstructed for the second value Zr2 of the reconstruction height, the second value Zr2 being distinct from the first value Zr1, or even for the second interval of values [Zr2min; Zr2max]. These ranges of values are determined experimentally depending on the quality of the obtained reconstructions.

From the reconstructed images, parameters of the nucleus 41A or of the cell 22 are determined. The nucleus 41A being elliptically shaped, these parameters are for example the length of the major axis of the ellipse, the area of the ellipse, the circularity of the ellipse, or further the ratio between the minor axis and the major axis of the ellipse.

The reconstruction system and method according to the invention have many advantages. They notably allow observation of a large number of diffracting objects 22 at a time, the number of cells 22 observed being for example of the order of 10,000 with a sensor array 28 having a surface area of a few square millimeters.

The reconstruction system 20 further has reduced bulk, as illustrated in FIGS. 1 and 2, the protective housing 38 notably having a diameter of the order of 10 cm and a height of the order of 2 cm.

The reconstruction system 20 may then be directly inserted into an incubator. This avoids having to remove the cells 22 from the incubator when their observation is desired, and the growth of the cells 22 is further not stopped during their observation.

Figure 5:
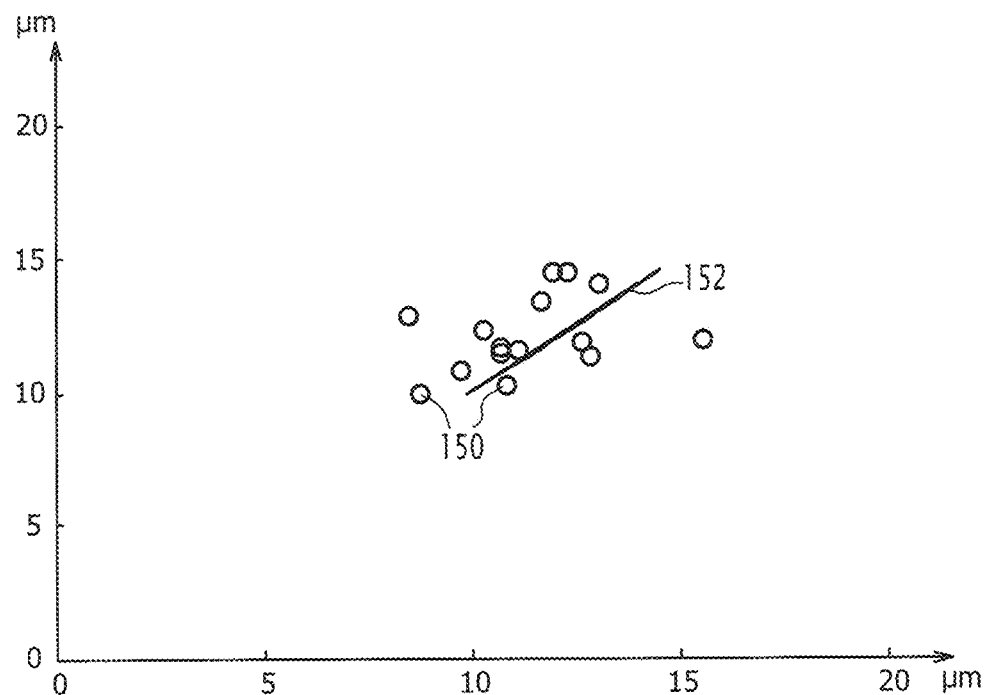
FIG. 5 is a cloud of points comparing the length of the largest side of diffracting objects with the shape of an ellipse, depending on whether this length is determined by means of the reconstruction method according to the invention or by use of a microscope.
Figure 6:
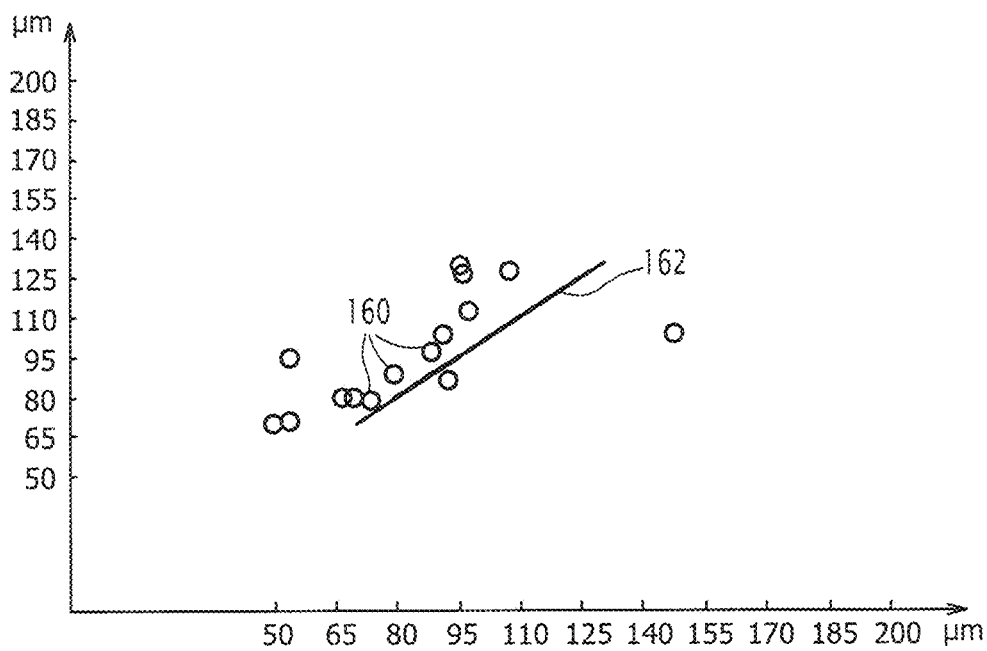
FIG. 6 is a cloud of points comparing the area of diffracting objects with the shape of an ellipse, depending on whether this area is determined by means of the reconstruction method according to the invention or by use of a microscope.

Further, by observing a large number of objects 22 at a time, it is possible to carry out statistical analysis of parameters of the reconstructed structures, as illustrated in FIGS. 5 and 6.

In FIG. 5, first circles 150 are illustrated for indicating the length of the major axis of the nucleus 41A for a plurality of observed cells 22, the axis of the abscissae corresponding to the length determined by means of the reconstruction method and of the construction system 20 according to the invention, and the axis of the ordinates corresponding to the length measured by means of the microscope. The observed results for the different cells 22 show that the values of the lengths of the major axis, determined by means of the reconstruction method according to the invention have good accuracy, since the first circles 150 are close to a first straight line 152 corresponding to the exact determination of said length of the major axis, the first straight line 152 being the representation of the affine identity function.

FIG. 6 is a view similar to that of FIG. 5 in the case when the parameter determined for the nuclei 41A is the area of the ellipse. In FIG. 6, second circles 160 are illustrated for indicating the area of the ellipse, the axis of the abscissae corresponding to the area determined by means of the reconstruction method according to the invention, and the axis of the ordinates corresponding to the area measured by means of the microscope.

FIG. 6 also shows that the determined parameters, i.e. the areas of the ellipses corresponding to the nuclei 41A of the different cells 22, are obtained with good accuracy, since the second circles 160 are close to a second line 162 corresponding to the exact determination of the areas of the nuclei 41A, the second line 162 being the representation of the affined identity function.

Figure 7:
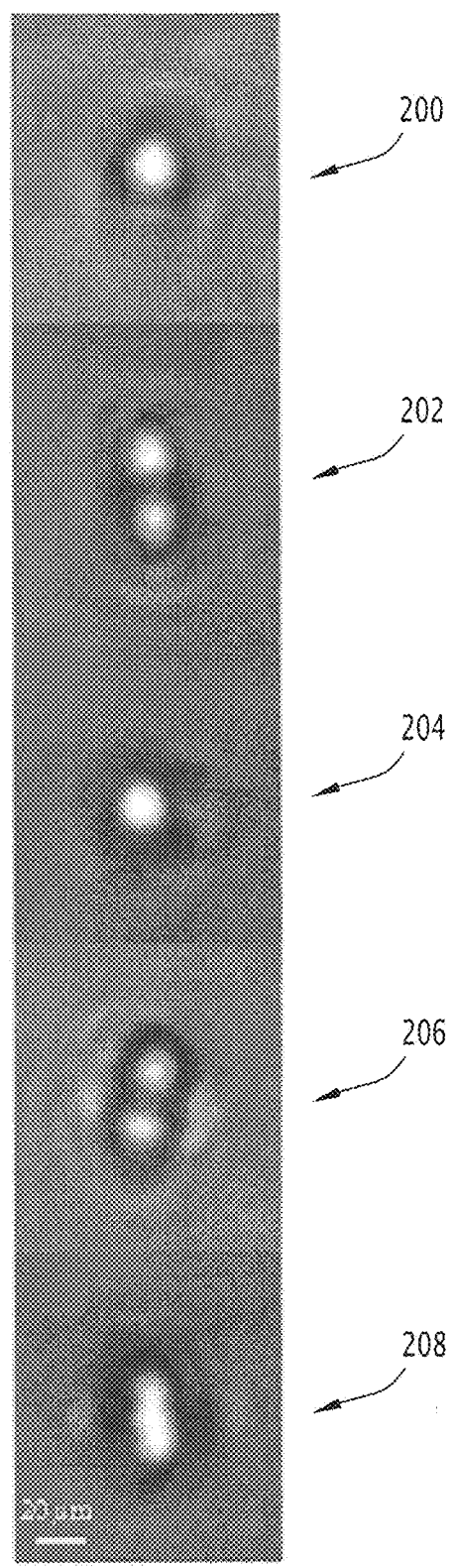
FIG. 7 is a view of five different images acquired by the photodetector of the reconstruction system of FIGS. 1 to 3, for five distinct diffracting objects, each including a first structure and a second structure.

FIG. 7 represents five diffraction patterns 200, 202, 204, 206, 208 obtained by means of the matrix photodetector 28 for five different diffracting objects 22.

FIG. 8 represents five first images of reconstructions 210, 212, 214, 216, 218 obtained for a reconstruction height Zr belonging to the first interval of values [Zr1min; Zr1max] from the measured intensity corresponding to the respective acquired images 200, 202, 204, 206, 208. More specifically, FIG. 8 illustrates the spatial distribution of the absorption. The images of reconstructions 210, 212, 214, 216, 218 obtained for the first interval of values then gives the possibility of observing the nuclei 41A of the different cells 22. The major axis of the nuclei 41A have a value of the order of 10 µm.

FIG. 9 represents five first reference images 220, 222, 224, 226, 228 obtained by means of the microscope for the nuclei 41A of the same cells 22.

Comparison of FIGS. 8 and 9 shows that the reconstruction method according to the invention is particularly effective since the nuclei 41A substantially have the same shape and the same dimensions in the case when their optical properties are reconstructed by means of the reconstruction method and in the case when they are observed by means of the microscope.

FIG. 10 illustrates five second reconstruction images 230, 232, 234, 236, 238 obtained for a reconstruction height Zr belonging to the second interval of values [Zr2min; Zr2max] from the measured intensity corresponding to the acquired images 200, 202, 204, 206, 208. More specifically, FIG. 10 represents the spatial distribution of the absorption. The second images of reconstructions 230, 232, 234, 236, 238 correspond to the cytoplasms 41B of the different cells 22. The cytoplasms 41B have a size of the order of 20 µm.

FIG. 11 illustrates the five second reference images 240, 242, 244, 246, 248 corresponding to the cytoplasms 41B of the same cells 22, obtained by means of the microscope.

Similarly to the comparison of FIGS. 8 and 9, comparison of FIGS. 10 and 11 shows that the reconstruction method according to the invention is particularly effective since the reconstructed cytoplasms 41B visible in FIG. 10, each have a shape and dimensions close to those of the cytoplasms 41B observed by means of the microscope, visible in FIG. 11.

In the exemplary embodiment of FIG. 8, the first interval of values [Zr1min; Zr1max] corresponds to the values of the reconstruction height Zr comprised between 280 µm and 350 µm, and in the exemplary embodiment of FIG. 10, the second interval of values [Zr2min; Zr2max] corresponds to the values of the reconstruction height Zr comprised between 410 µm and 450 µm, with the second distance D2 substantially equal to 700 µm in both examples.

It should be noted that other tests were carried out for different values of the second distance D2 in order to determine the values of the first and second intervals [Zr1min; Zr1max], [Zr2min; Zr2max] allowing reconstruction of the nucleus 41A and respectively of the cytoplasm 41B for these values of the second distance D2.

When the second distance D2 is substantially equal to 500 µm, the first interval of values [Zr1min; Zr1max] corresponds to the values of the reconstruction height Zr comprised between 240 µm and 280 µm and the second interval of values [Zr2min; Zr2max] corresponds to those comprised between 380 µm and 420 µm.

When the second distance D2 is substantially equal to 2,000 µm, the first interval of values [Zr1min; Zr1max] corresponds to the values of the reconstruction height Zr comprised between 1,200 µm and 1,300 µm, and the second interval of values [Zr2min; Zr2max] corresponds to those comprised between 1,400 µm and 1,500 µm.

Figure 12:
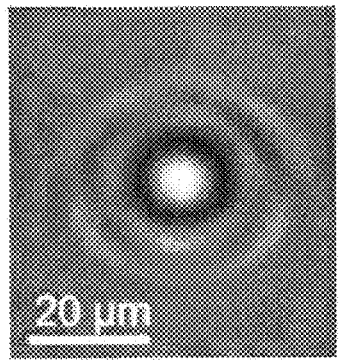
FIG. 12 is a view of the image acquired by the photodetector of the reconstruction system of FIGS. 1 to 3 for another diffracting object.
Figure 13:
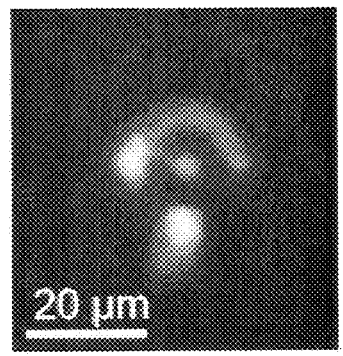
FIG. 13 is a view of the image of the object of FIG. 12, the absorption of which is reconstructed by means of the reconstruction system according to the invention.
Figure 14:
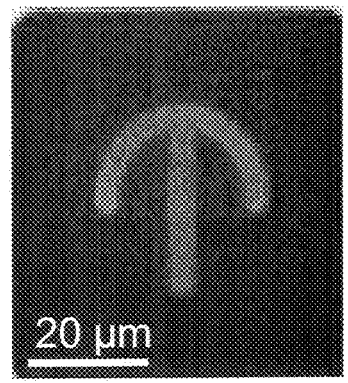
FIG. 14 is a view of a reference image of the object of FIG. 12, this image representing a substrate including a functionalized area which is favorable to cell adhesion.

FIG. 12 illustrates a diffraction pattern directly acquired by the photodetector 28 for another diffracting object 22, FIG. 13 illustrates the reconstruction of this object 22 for a reconstruction height Zr strictly smaller than the second distance D2 between the medium 24 and the photodetector 28, and FIG. 14 illustrates a reference image of the diffracting object 22, obtained by means of the microscope. More specifically, FIG. 13 represents the spatial distribution of the absorption.

There again, comparison of FIGS. 13 and 14 shows that the reconstruction method according to the invention gives the possibility of obtaining satisfactory results since the dimensions and the shape of the reconstructed object, visible in FIG. 13, are very close to those of the reference image, visible in FIG. 14. This reference image illustrates a chemically functionalized substrate for promoting adhesion of cells according to a predetermined shape. Because of this functionalization, the cytoskeleton of the cell (cell NIH 3T3) assumes a particular shape, this shape being consistent with the shape observed in FIG. 13.

The reconstruction system 20 and the reconstruction method according to the invention therefore allow reconstruction of the optical properties of the objects 22 in a highly satisfactory way, the result being close to those observed by means of a microscope, and this even for objects having a diameter of less than about 20 μm.

The reconstruction system 20 and the reconstruction method according to the invention further allow the observation of a large number of objects 22 at a time. The reconstruction system 20 further has reduced bulk, which allows it to be directly inserted into an incubator, and then greatly facilitates the observation operations and for reconstruction of the optical properties of the objects 22.

Thus, it is realized that the reconstruction system 20 and the reconstruction method according to the invention allow reconstruction of the optical properties of particles 22, the size of which is less than about 20 μm, such as cells with a diameter of the order of 10 μm, bacteria with the diameter of the order of 1 μm, or further viruses.

The following example shows how a reconstructed image is obtained, representing the modulus of the absorption $a(x,y)$, at a given reconstruction height z, according to the image $I(x,y)$ acquired by the matrix photodetector 28.

In the example of FIGS. 15 to 20, the second distance D2 between the medium 24 and the matrix photodetector 28 along the vertical direction Z is substantially equal to 500 μm, and the diffracting objects 22, also called diffracting elements, are each in the form of a sphere having a diameter of the order of 10 μm.

Figure 15:
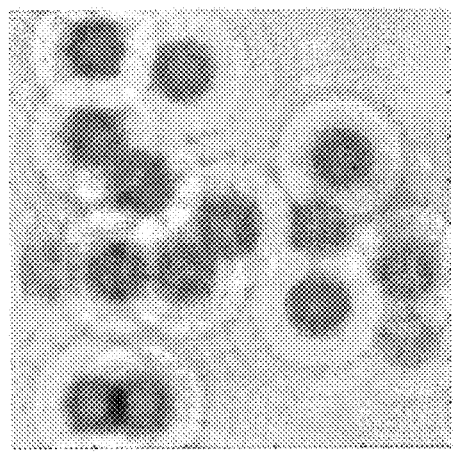
FIGS. 15 to 20 illustrate an example for applying an algorithm for obtaining a reconstruction image, representing the modulus of the complex absorption, at a given reconstruction height and according to an image acquired by the photodetector of the reconstruction system of FIGS. 1 to 3.

FIG. 15 illustrates an image of the diffracting elements 22 acquired by the photodetector 28, the grey level of this image representing the absorption (i.e. the modulus of the complex absorption) of each diffracting element 22.

Figure 16:
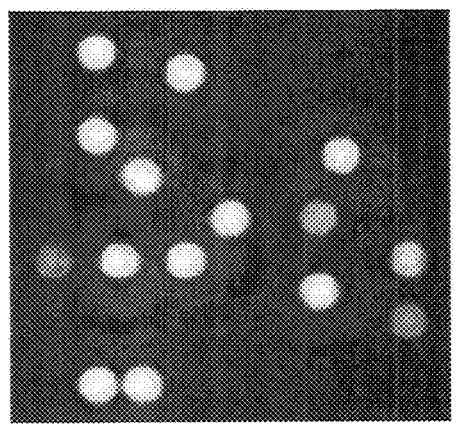
Figure 17:
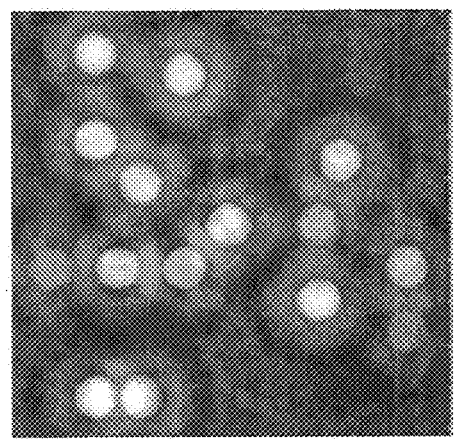

FIG. 16 illustrates a simulation of the image acquired by the photodetector 28, i.e. of the intensity I measured by the photodetector 28. By applying the reconstruction algorithm described by equation (1), i.e. by performing the convolution $I * h_{-z}$ operation described earlier, a complex reconstructed image is obtained, the modulus of which is illustrated in FIG. 17. The spatial distribution of the absorption is observed therein, onto which is superposed a noisy signal, usually designated by the term of "twin image" and noted as ti. The twin image is, for example, described in the article "Phase retrieval algorithms: a comparison" from J R Fienup, published in August 1982 in the journal Applied Optics, Volume 21, Number 15.

Methods for reducing the influence of the twin image are known to one skilled in the art and have been described in the literature in the 2000s. Thus it is possible to improve this representation of the reconstructed image, so as to reduce the contribution of the twin image signal and then obtain a spatial distribution of the absorption at the distance z of the photodetector 28, in the direction of the light source 26.

The following example is an example of an applied algorithm. For this, it is considered that the convolution of the twin in a signal with the function $h_{2z}$ leads to an estimation of the complex opacity a. Also, it is considered that the convolution of the complex opacity a with the function $h_{2z}$ leads to an estimation of the twin image ti. In other words, it is considered that $a*h_{2z}=ti$ and $ti*h_{2z}=a$.

From the reconstructed complex image $I*h_{-z}$, an iterative algorithm is applied, for reducing the influence of the twin image noise on the thereby reconstructed image. This algorithm comprises the following steps:

storing in memory an initial image, noted as $Im_{initial}$, such that $Im_{initial}=I*h_{-z}$;

beginning an iteration I;

amplitude thresholding the image $Im_i$, the threshold for example being greater than the average value of the twin image, so as hide the pixels below the threshold (this thresholding is performed automatically, e.g., using a computer, or manually; during the first iteration, why has the identity $Im_{i=1}=Im_{initial}$; it is considered that the thereby thresholded image $Im_i$ is a good estimation of the opacity a at iteration i, noted as $a_i$);

estimating the twin image signal at iteration i: $ti_i=Im_i-a_i$;

storing in memory a new image $Im_{i+1}=ti_i*h_{2z}$; and applying the next iteration, the iterative algorithm is stopping according to a determined stopping criterion (such a criterion is for example a predetermined number of iterations or further a comparison between $Im_i$ and $a_i$ or between $Im_i$ and $Im_{i-1}$).

At the end of the iterative algorithm, an image Im is obtained, which corresponds to a correct estimation of the complex opacity a. By representing the modulus of this complex opacity, the distribution of the absorption is obtained at the relevant distance z. An application of this algorithm is illustrated in FIGS. 17 to 20.

FIG. 17 illustrates the modulus of the complex function $Im_1=I*h_{-z}$, I being at the image acquired by the photodetector 28, illustrated in FIG. 16, which is the starting image of the algorithm.

Figure 18:
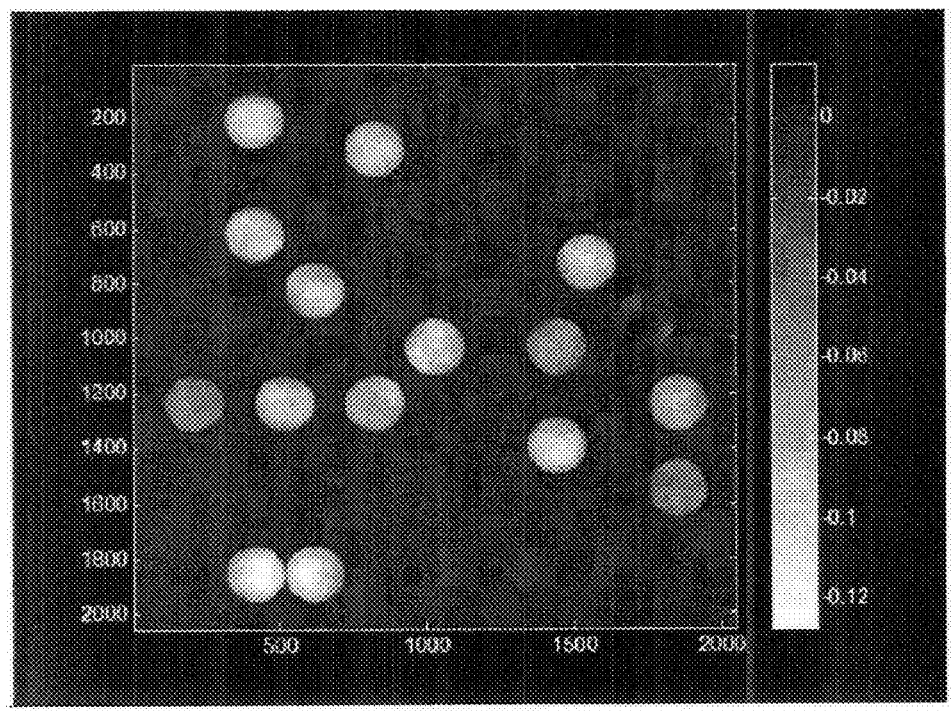
Figure 19:
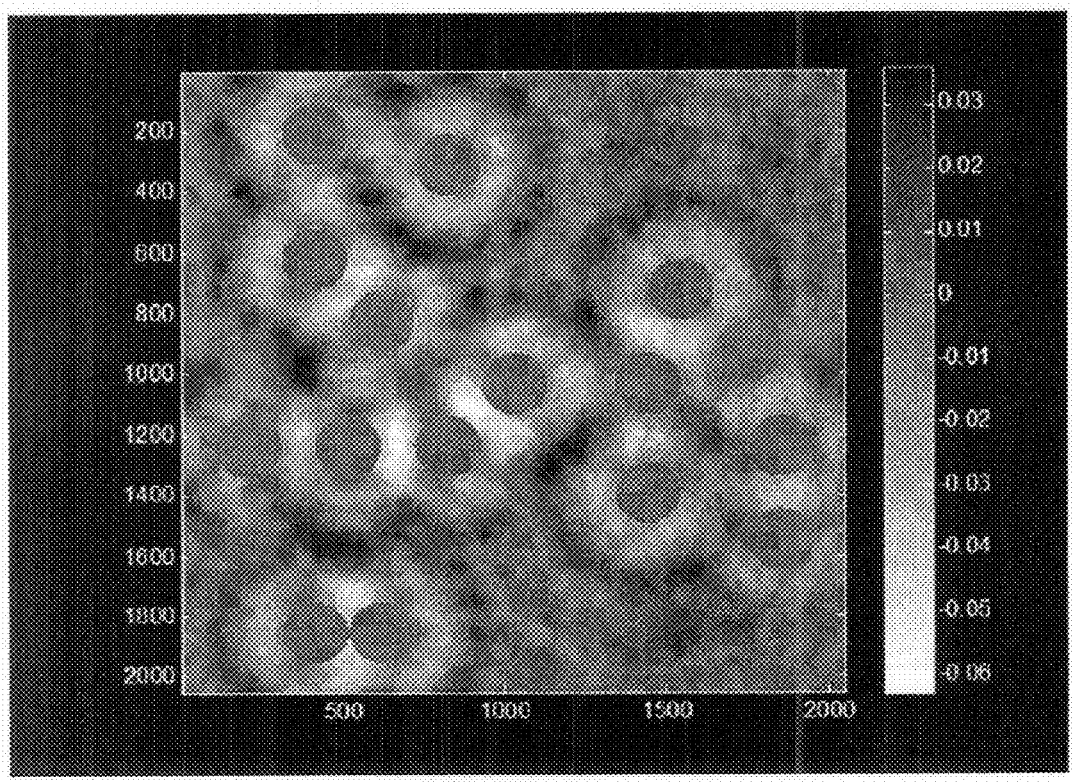

FIG. 18 illustrates the image of FIG. 17 after amplitude thresholding, so as to hide the pixels below said threshold. This is an estimation of the complex opacity $a_{i=1}$ FIG. 19 illustrates the modulus of the function $t_i$ $_{i=1}=Im_{i=1}-a_{i\ i=1}$. This is an estimation of the twin image noise at the first iteration.

Figure 20:
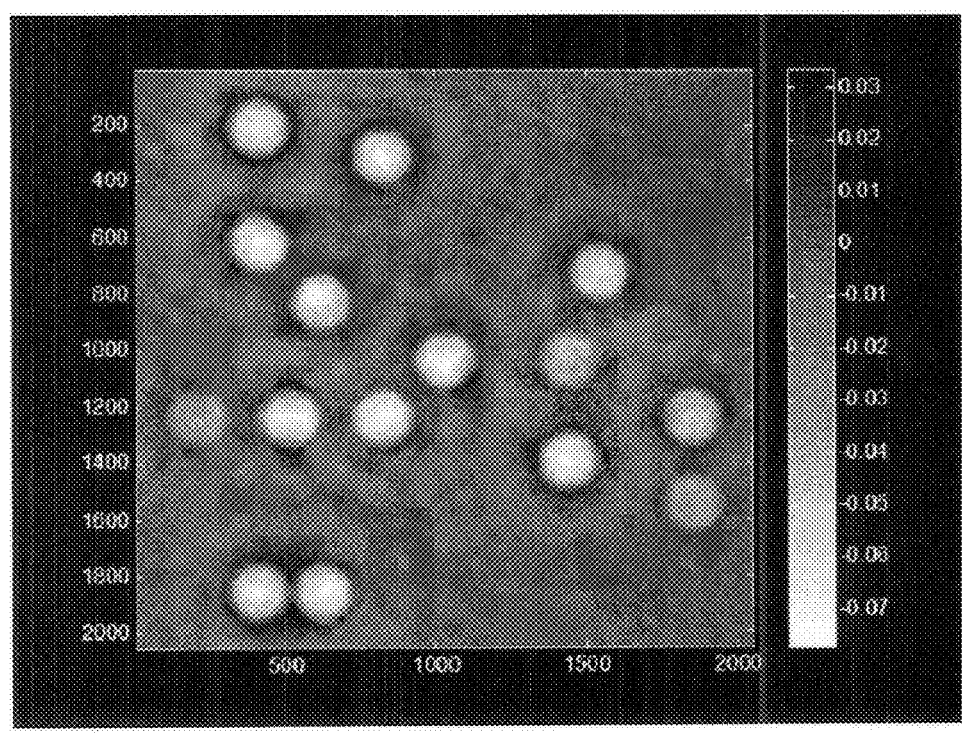

FIG. 20 illustrates the modulus of the function $Im_{i=2}=ti_{i=1}*h_{2z}$. Which corresponds to the image used as a basis for the second iteration. It is then seen that between the images $Im_{i=1}$ (FIG. 17) and $Im_{i=2}$, (FIG. 20), i.e. between two successive iterations, the twin image signal has been considerably reduced, which gives the possibility of better distinguishing the spatial distribution of the absorption at the reconstruction height, FIG. 15 being used as a reference image.

What is claimed is:

1. A method for reconstructing optical properties of at least one diffracting object immersed in a liquid medium using a reconstruction system that comprises a spatially coherent light source and a matrix photodetector, wherein the liquid medium is delimited by a transparent surface and the at least one diffracting object is in contact with the transparent surface, and wherein the liquid medium and the matrix photodetector are separated by a distance along a vertical direction, the method comprising:

illuminating the liquid medium with the spatially coherent light source;

measuring, with the matrix photodetector, an intensity of at least one diffraction pattern transmitted by the illuminated medium along a vertical direction, wherein each diffraction pattern corresponds to waves diffracted by the at least one diffracting object upon illumination of the medium; and reconstructing the optical properties of the at least one diffracting object at a reconstruction height according to a reconstruction algorithm from the measured intensity of the at least one diffraction pattern, wherein the reconstruction height is a parameter of the reconstruction algorithm that is distinct from the distance between the liquid medium and the matrix photodetector along the vertical direction, and wherein the reconstruction height has a value selected to be less than the distance between the liquid medium and the matrix photodetector along the vertical direction.

2. The method according to claim 1, wherein the value of the reconstruction height is less than 0.9 times the distance between the medium and the photodetector.

3. The method according to claim 1, wherein the value of the reconstruction height is less than 0.8 times the distance between the medium and the photodetector.

4. The method according to claim 1, wherein the reconstruction algorithm satisfies the following equation:

$$I(x, y) * h_{-Zr}(x, y) = e^{j2\pi \frac{-Zr}{\lambda}} \left( 1 - a(x, y) - e^{j2\pi \frac{2Zr}{\lambda}} \cdot a^*(x, y) * h_{-2Zr}(x, y) \right)$$

wherein I is the intensity measured by the matrix photodetector, x, y are the coordinates in a plane perpendicular to the vertical direction, * is the convolution product, Zr is the reconstruction height, λ is the wave length of the light source, j is the unit imaginary number, a is the complex opacity function of an object, a* represents the conjugate complex of a, and $h_z$ is defined by the following equation:

$$h_z(x, y) = \frac{1}{j\lambda z} e^{j2\pi \frac{z}{\lambda}} \exp\left( j\pi \frac{x^2 + y^2}{\lambda z} \right).$$

5. The method according to claim 1, wherein the optical properties of the at least one diffracting object are reconstructed for different values of the reconstruction height.

6. The method according to claim 5, wherein the at least one diffracting object includes a first structure and a second structure, and wherein the optical properties of the first structure are reconstructed for a first value of the reconstruction height, and the optical properties of the second structure are reconstructed for a second value of the reconstruction height, the second value being distinct from the first value.

7. The method according to claim 6, wherein the at least one diffracting object is a cell including a nucleus and a cytoplasm, and wherein a representative image of the nucleus is reconstructed for a first interval of values and a representative image of the cytoplasm is reconstructed for a second interval of values, the second interval being distinct from the first interval.

8. The method according to claim 7, wherein the second interval is disconnected from the first interval.

9. The method according to claim 8, wherein the values of the first interval are less than the values of the second interval.

10. The method according to claim 9, wherein the distance between the liquid medium and the matrix photodetector along the vertical direction is substantially equal to 500 μm, the first interval comprises values between 240 μm and 280 μm, and the second interval comprises values between 380 μm and 420 μm.

11. The method according to claim 1, wherein the intensity of each diffraction pattern is directly measured with the matrix photodetector, in the absence of any magnification optics placed between the medium and the photodetector.

12. The method according to claim 1, wherein the reconstructed optical properties comprises an absorption of the at least one diffracting object, a phase lag produced by the at least one diffracting object, or a combination thereof.

13. A system for reconstructing optical properties of at least one diffracting object immersed in a liquid medium, the liquid medium being delimited by a transparent surface, the at least one diffracting object being in contact with the transparent surface, the reconstruction system comprising:

a spatially coherent light source capable of illuminating the medium;

a matrix photodetector separated from the liquid medium by a distance along a vertical direction, wherein the matrix photodetector is capable of measuring an intensity of at least one diffraction pattern transmitted by the illuminated medium along a vertical direction, and wherein said at least one diffraction pattern corresponds to waves diffracted by the at least one diffracting object upon illumination of the medium; and a means for reconstructing the optical properties of the at least one diffracting object at a reconstruction height according to a reconstruction algorithm from the measured intensity of the at least one diffraction pattern, wherein the reconstruction height is a parameter of the reconstruction algorithm that is distinct from the distance between the liquid medium and the matrix photodetector alongthe vertical direction, and wherein the reconstruction height has a value selected to be less than the distance between the liquid medium and the matrix photodetector along the vertical direction.

14. The system according to claim 13, wherein the value of the reconstruction height is less than 0.9 times the distance between the medium and the photodetector.

15. The system according to claim 13, wherein the value of the reconstruction height is less than 0.8 times said distance between the medium and the photodetector.

16. The system according to claim 13, wherein the light source includes a light emitting diode and a diaphragm placed in contact with the light emitting diode.

17. The system according to claim 13, wherein the matrix photodetector is a CCD sensor or a CMOS sensor.

* * * * *